United States Patent [19]
Forssmann et al.

[11] Patent Number: 5,461,142
[45] Date of Patent: Oct. 24, 1995

[54] PHOSPHORYLATED DERIVATIVES OF CARDIODILATIN/ANF PEPTIDES

[75] Inventors: Wolf-Georg Forssmann, Im Langgewann 93, D-6900 Heidelberg 1; Michael Gagelmann, Schriesheim; Dieter Hock, Neckarbischofsheim, all of Germany

[73] Assignees: Pharma Bissendorf Peptide GmbH, Hanover; Wolf-Georg Forssmann, Heidelberg, both of Germany; a part interest

[21] Appl. No.: 95,049

[22] Filed: Jul. 22, 1993

Related U.S. Application Data

[63] Continuation of Ser. No. 499,251, May 10, 1990, abandoned.

[30] Foreign Application Priority Data

Nov. 7, 1987 [DE] Germany .......................... 37 37 917.8

[51] Int. Cl.[6] .............................. A61K 38/22; C07K 1/04; C07K 1/113; C07K 14/58
[52] U.S. Cl. ..................... 530/324; 514/7; 514/12; 514/21; 530/334; 530/345; 530/352; 530/408; 530/410; 930/50; 930/DIG. 554
[58] Field of Search ..................... 514/7, 21, 12; 530/324, 345, 350, 352, 380, 408, 410, 334; 930/50, DIG. 553, DIG. 554, DIG. 555

[56] References Cited

U.S. PATENT DOCUMENTS

4,508,712  4/1985  Needleman ................. 514/11

FOREIGN PATENT DOCUMENTS

147193   7/1985  European Pat. Off. .............. 530/324
0182984  6/1986  European Pat. Off. .
3443257  5/1986  Germany .

OTHER PUBLICATIONS

Bloch et al, "Proatrial Natriuretic Factor is Phosphorylated by Rat Cardiocytes in Culture". *J. Biol. Chem.* 262(21), Jul. 25, 1987, pp. 9956–9961.

Olins et al, "Phosphorylation of high-and low-molecular-mass atrial natriuretic peptide analogs . . . ". *FEBS Lett.* 224(2), Nov. 1987, pp. 325–330.

Rittenhouse et al, "Phosphorylation of Atrial Natriuretic Peptides by Cyclic AMP-dependent Protein kinase." *J. Biol. Chem.* 261(17), Jun. 15, 1986, pp. 7607–7610.

Rittenhouse et al, "Phosphorylation in Situ of Atrial Natriuretic Peptide Prohormone . . . ". *J. Biol. Chem.* 263(8), Mar. 15, 1988, pp. 3778–3783.

Chemical Abstracts, vol. 105, 1986, p. 138, No. 73295w.
Chemical Abstracts, vol. 108, 1988, p. 148, No. 49972f.
Chemical Abstracts, vol. 108, 1988 p. 156, No. 144184j.
Chemical Abstracts, vol. 107, 1987, p. 157, No. 127948y.

*Primary Examiner*—Jeffrey E. Russel
*Attorney, Agent, or Firm*—Jacobson, Price, Holman & Stern

[57] ABSTRACT

Described are derivatives of the precursor peptide of the cardiodilatin/atrial sodiuretic factor (CDD-ANF) or fragments thereof which comprise at least the amino acid sequence of alpha-hANaP. The derivatives according to the present invention are compounds of the formula (I)

(Abstract continued on next page.)

X is a phosphate or thiophosphate group. R is $NH_2$ or a peptide fragment from the amino acid sequence of gamma-hANaP. Radio-labelled derivatives are also possible. A method for the qualitative and/or quantitative determination of peptides containing the sequence of alpha-hANaP and a use of the compounds having the formula (I) as medicaments for various vaso- and renal related disorders are further described.

5 Claims, 7 Drawing Sheets

PHOSPHORYLATED DERIVATIVES OF CARDIODILATIN/ANF PEPTIDES

This application is a continuation of U.S. application Ser. No. 07/499,251 filed May 10, 1990 now abandoned.

The invention relates to derivatives of the precursor peptide of the cardiodilatin/atrial sodiuretic factor pre-pro-gamma-hANaP (CDD-ANF) or fragments thereof which have at least the amino acid sequence of the alpha-hANaP. Furthermore, the invention relates to a process for the preparation of said derivatives and the use thereof.

Cardiodilatin, alpha-hANaP and further sodiuretically/diuretically active peptides are derived from a common precursor peptide, the pre-pro-gamma-hANaP which comprises 151 amino acids.

Figure 1:
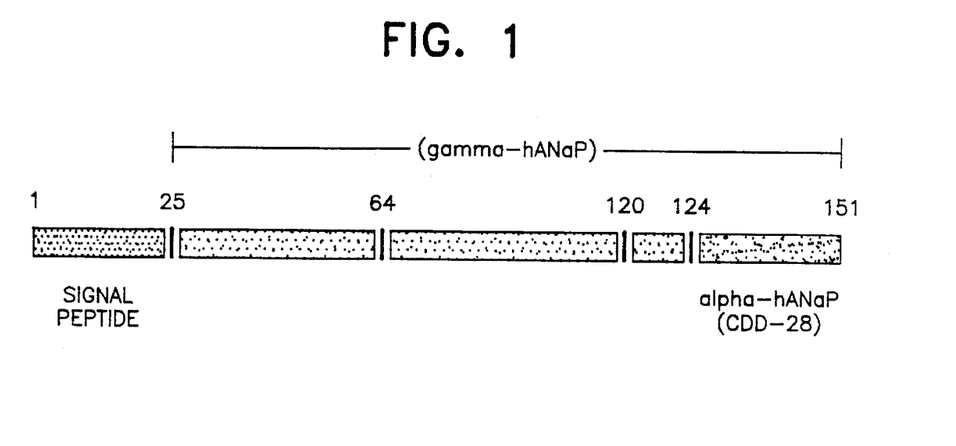
FIG. 1 shows a schematic representation of the sequences for pre-pro-gramma nANaP.
Figure 2:
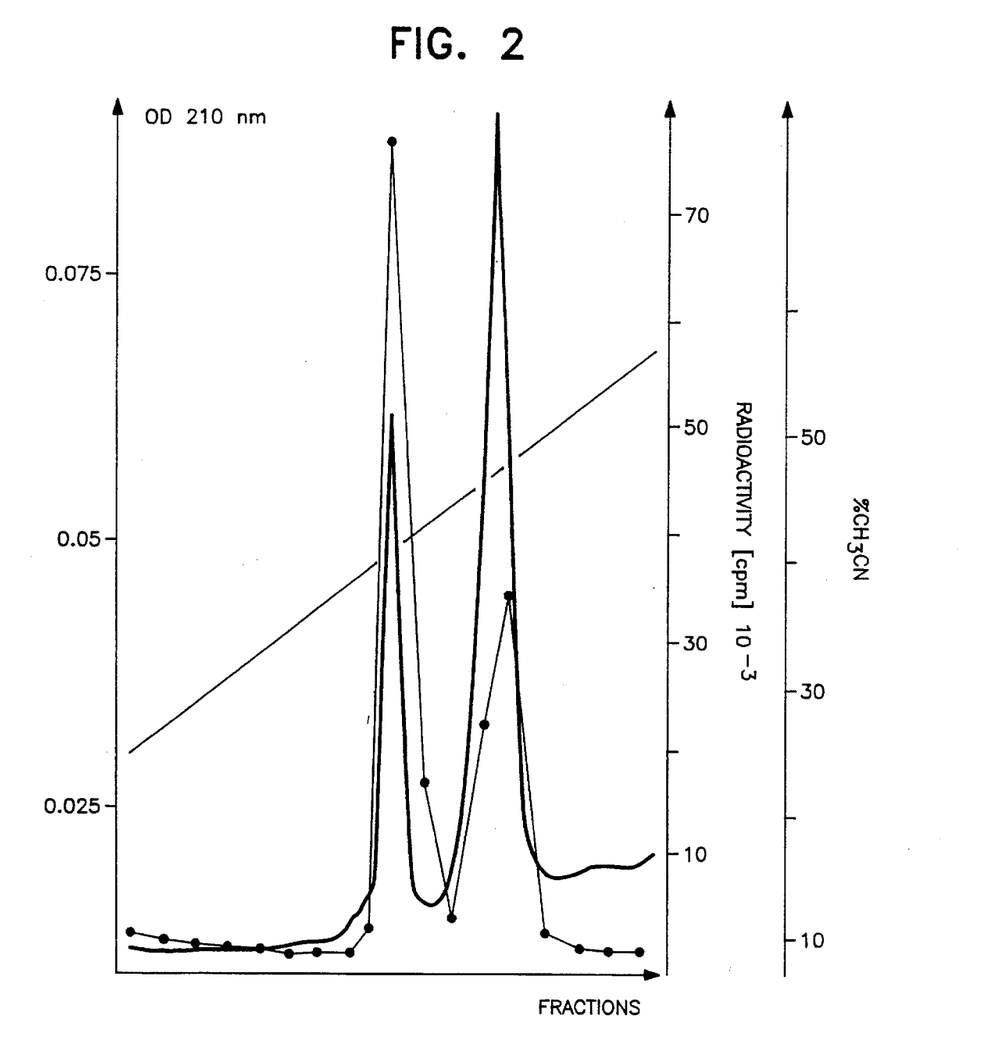
FIG. 2 shows an elution pattern of phosphorylated alpha-hANAP (CDD-28) and CDD-88.
Figure 3:
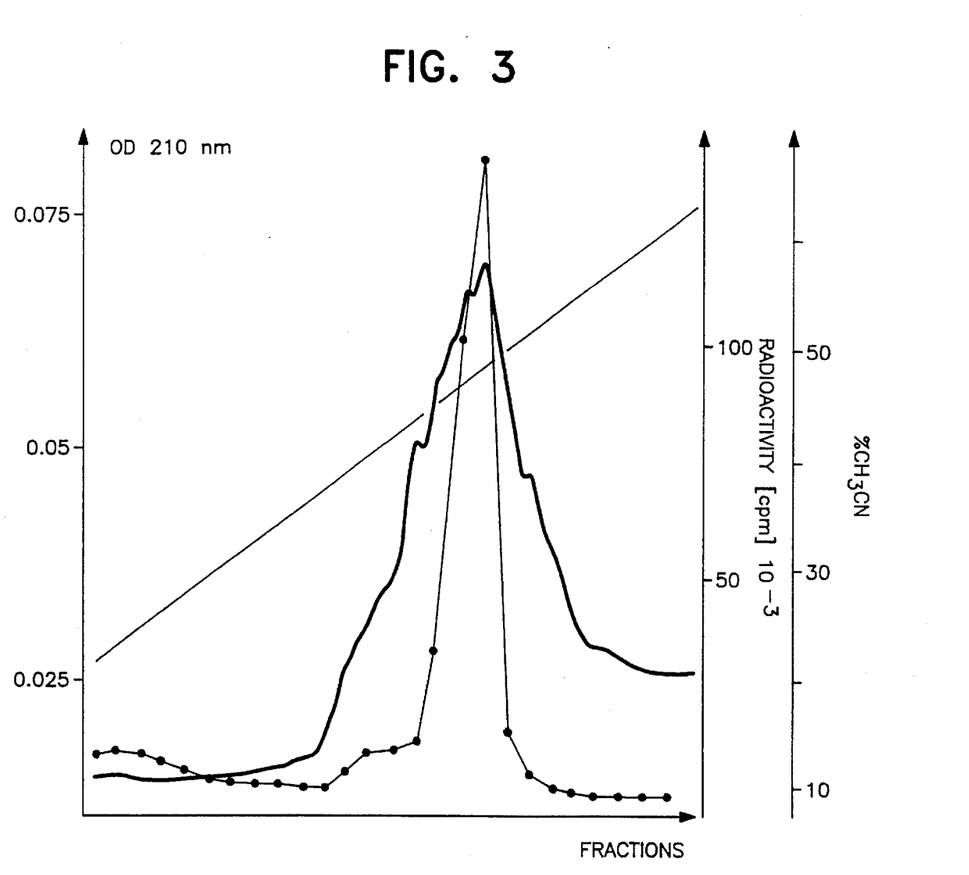
Figure 4:
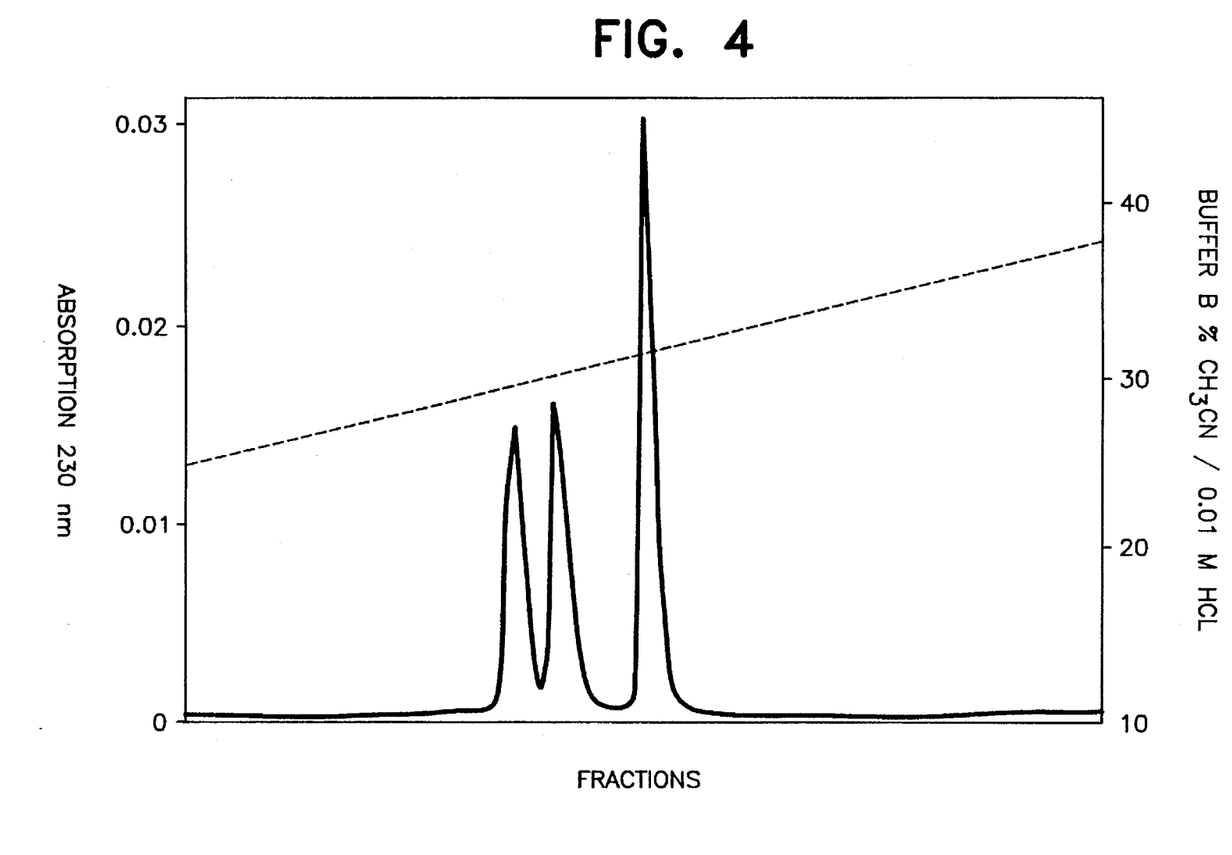
FIG. 4 shows the separation of 2 µg each of unphosphorylated alpha-hANaP (CDD-28), CDD-32 (urodilatin) and phosphorylated alpha-hANaP. The samples were mixed and separated by RP-HPLC (Reversed Phase HPLC). The eluant consisted of a linear gradient of acetonitrile/0.01% HCl as buffer B and 0.01% HCl as buffer A. The initial concentration of buffer B was 20%; the column was developed with a flow rate of 0.7 ml/min at a continuous addition of buffer B (0.5%/min). The signal measured was the absorption at 230 nm. The separation conducted under these conditions first results in an elution of unphosphorylated alpha-hANaP, followed by phosphorylated alpha-hANaP, and finally in an elution of CDD-32 (urodilatin).
Figure 5:
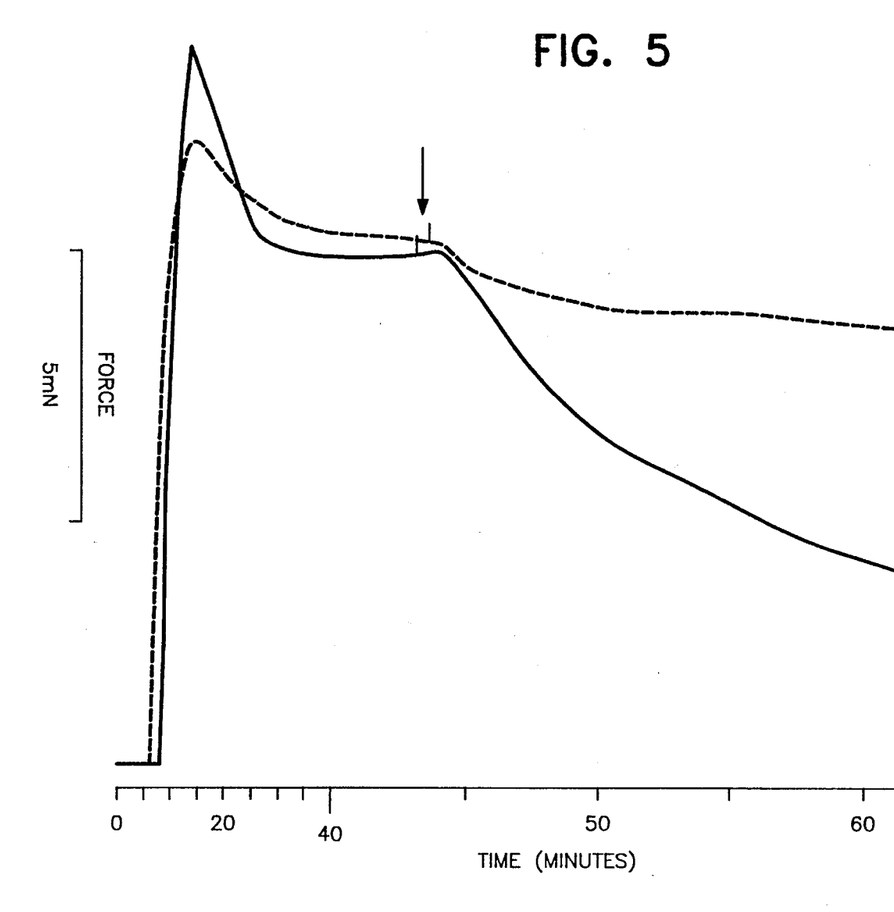
Figure 6:
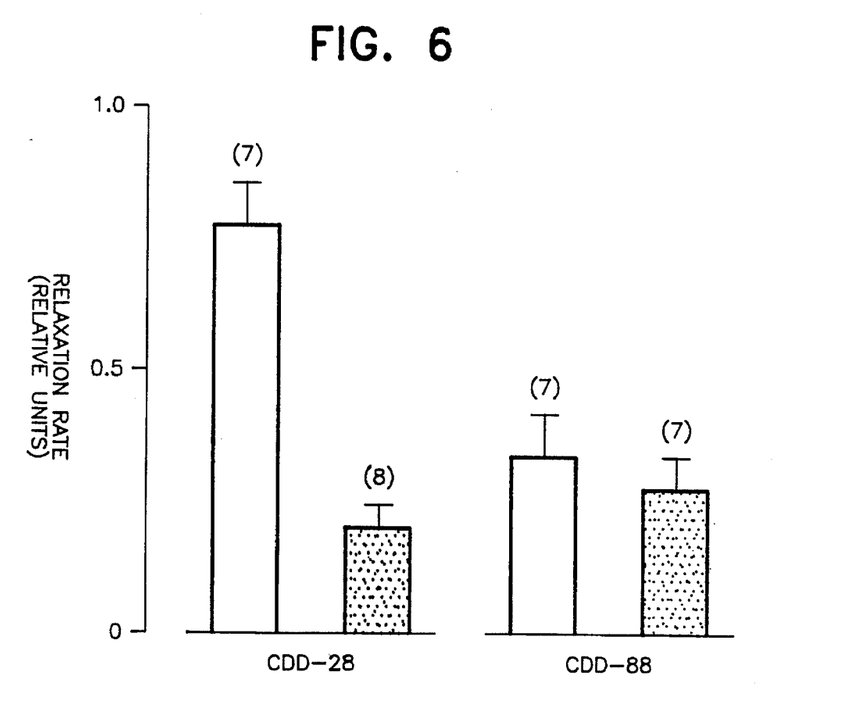
FIG. 6 represents a summary of a number of experiments with phosphorylated CDD-28 and CD-88 and unphosphorylated CDD-28 and CD-88. In both cases, the concentrations were from 0.3 to $0.6 \times 10^{-9}$M. In the graph, the relative rates of relaxation and the standard errors for unphosphorylated (open rectangles) as well as phosphorylated (shaded rectangles) CDD-28 and CDD-88 peptides are shown (the figures atop of the rectangles denote the number of experiments carried out).
Figure 7:
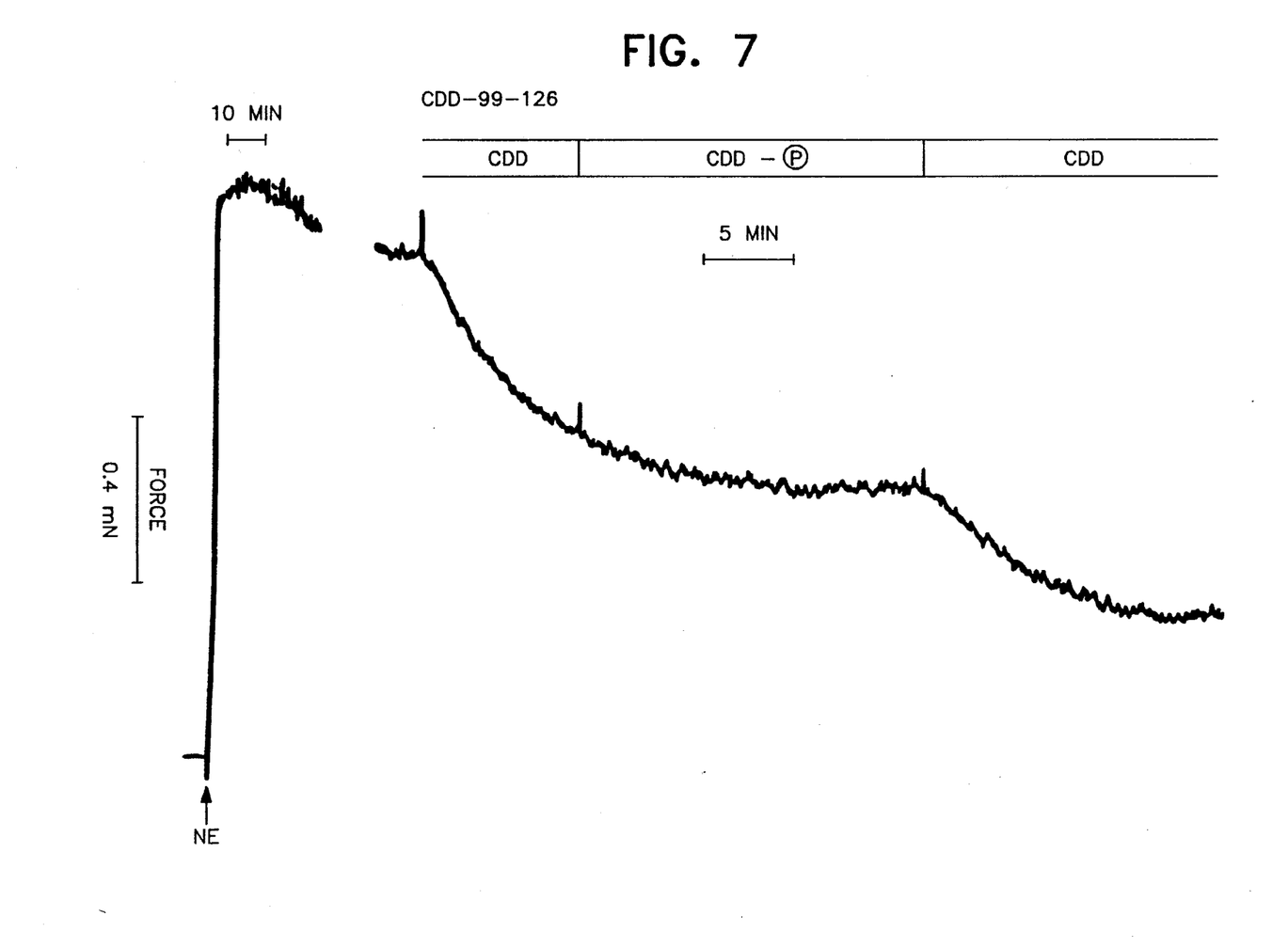
FIG. 7 shows the response of rabbit aorta muscle strips to a stepwise addition of unphosphorylated, phosphorylated, and again unphosphorylated alpha-hANaP (CDD-28). Each of the compounds was added so that its final concentration in the test bath was $0.3 \times 10^{-9}$M. Pre-contracted muscle strips relaxed to some degree upon the addition of unphosphorylated alpha-hANaP. The addition of phosphorylated alpha-hANaP {CDD-Ⓟ}, however, shows an effect next to nothing. The muscle relaxation continues only after a further addition of unphosphorylated alpha-nANaP.
Figure 8:
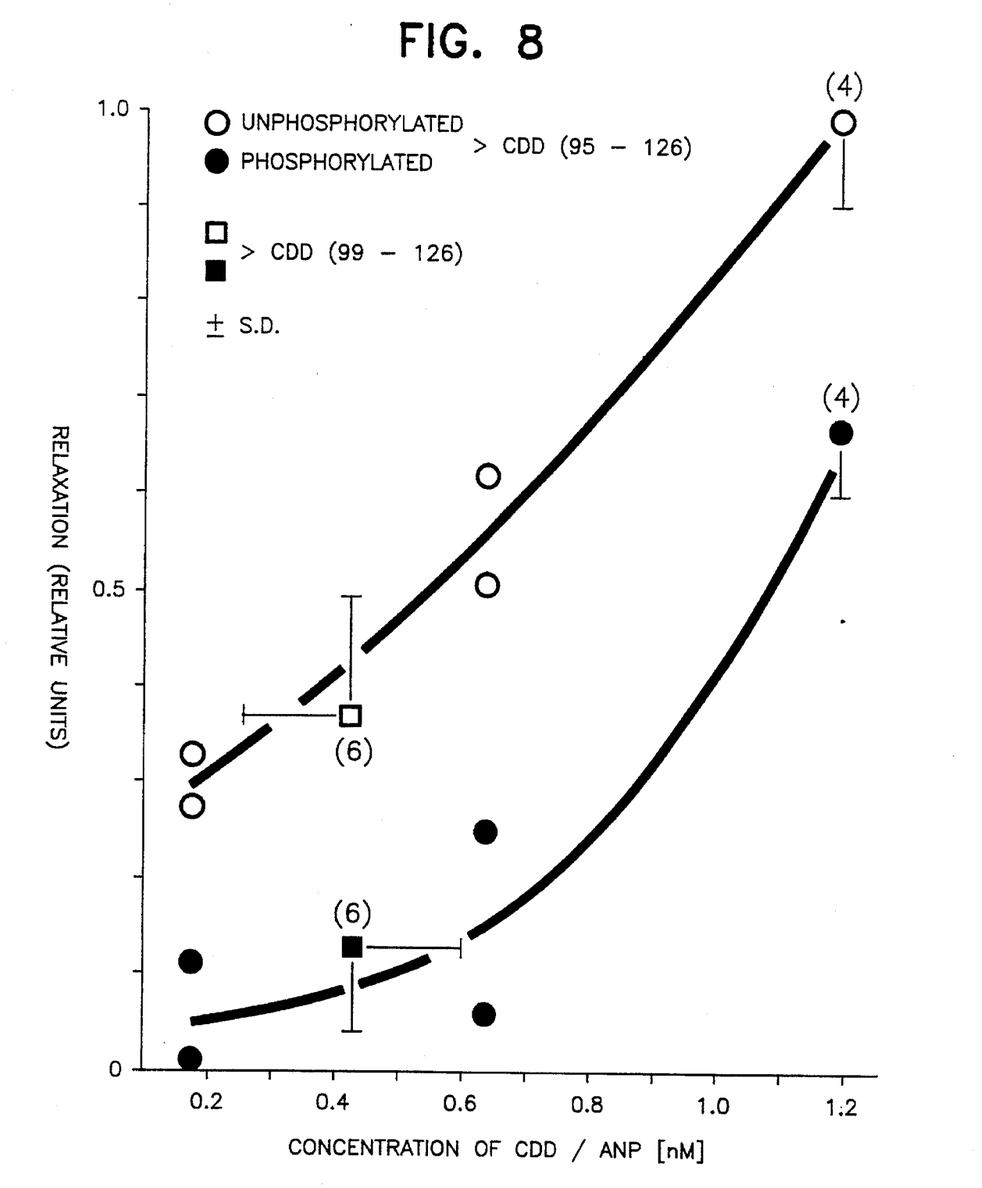

As seen in FIG. 1, positions 1–25 of the amino acid sequence are considered as the signal peptide, whereas the positions 25–151 represent the gamma-hANaP, which inter alia in the region of the C-terminal end (positions 124–151) is identical with the alpha-hANaP (Oikawa, S. et al., "Nature" 309 (1984), 724–726; Nakayama, K. et al., "Nature" 310 (1984), 699–701). However, the numbering as used hereinbelow will leave the signal peptide out of consideration. Thus, there is valid for gamma-hANaP an amino acid sequence of positions 1–126, and for alpha-hANaP an amino acid sequence of positions 99–126 (CDD-28).

Further peptide fragments of the gamma-hANaP have been described, namely fragments comprising the amino acids 39–126 (CDD-88) and the amino acids 95–126 (CDD-32). The latter possesses at its N-terminus 4 amino acids more than CDD-28 and is also designated as urodilatin. Blood pressure-regulating activities are attributed to the atrial peptides due to the stimulation of sodiuresis, diuresis and relaxation of the smooth musculature. The DE-OS 34 43 257 describes alpha-hANaP as an agent for treating various diseases such as cardial insufficiency, oliguric renal failure, blood pressure dysregulation and ascites.

Peptides, and especially endogenous peptides, are degraded in vivo by way of enzymatic reactions. Therefore it is possible only with difficulty to administer the respective therapeutically effective dosage over an extended period of time, and more particularly so, since a higher dose intended to compensate the degradation of the peptide is inapplicable in most cases because of the high physiological activity of the endogenous messenger substances. Thus, what is desirable is that a form of the biologically active peptide is provided in which it has a biological activity which is as low as possible, but which is converted into the physiologically active form by endogenous acceptable modifying reactions.

Due to the importance of the cardiodilatin or of the atrial sodiuretic factor, respectively, it is important to have a method for safe analytical determination of the actual instant concentration of the corresponding physiologically active compound, in order to qualitatively detect and to quantitatively determine the active peptides and/or peptide fragments.

A known biochemical principle of the modulation of the action of biomolecules, such as enzymes and receptors, is based on phosphorylating and dephosphorylating reactions.

Rittenhouse, J. et al., J. Biol. Chem. 261 (1986), 7607–7610, describes the phosphorylation of synthetic peptides having the amino acid sequence of $Arg^{101}$—$Tr^{126}$ of the alpha-hANaP by means of c-AMP-dependent proteinkinase, which requires Arg—Arg—X—Ser as the recognition sequence. Therein it has also been described that the synthetic peptide has a Michaelis constant of $K_m=0.5$ μM. The synthetic peptide phosphorylated at $Ser^{104}$ in vitro possesses a physiological activity, which is manifested in the stimulation of the Na/K/Cl cotransport in cultivated vascular cells in the smooth musculature. Bloch, K. D. et al., J. Biol. Chem. 262 (1987), 9956–9961, on the other hand, describes experiments wherein in primary cultures of cardiocytes of newborn rats a serin moiety in a fragment obtained by trypsin degradation (positions 26–67 the gamma-hANaP) of the pro-ANF (gamma-hANaP) is phosphorylated in vivo. These findings speak in favor of gamma-hANaP not being phosphorylated within that range which is removed as alpha-hANaP. Thus, the synthetic phosphorylated peptides $Arg^{101}$—$Tr^{126}$ $Gly^{196}$—$Tyr^{126}$ (Rittenhouse et al.) do not have any natural physiological significance.

It is an object of the invention to provide chemical compounds which allow an easy qualitative and quantitative determination of peptides containing the sequence of the active principle of the gamma-hANaP, namely the alpha-hANaP (positions 98–126). It is another object of the invention to provide chemical compounds from which by means of an endogenous modification an active substance is formed, while the parent compound itself has no or only little physiological activity. It is a further object of the invention to provide a method by means of which the presence of sodiuretic-atrial peptides can be qualitatively and quantitatively determined.

Said objects are attained by a compound having the formula I wherein X is a phosphate group or thiophosphate group and R is either a residue —H or a peptide fragment from the amino acid sequence of gamma-hANaP.

The compound of the formula I according to the invention can be obtained in a particularly elegant way by the enzymatic phosphorylation of the corresponding starting compound of the formula II with the respective nucleotides. According to a preferred embodiment, c-AMP-dependent proteinkinase or its catalytic subunit as the enzyme and adenosine-5'-triphosphate (ATP) or adenosine-5'-(gamma-thio)triphosphate as the nucleotide are reacted with the compound of the formula II in a per se known manner. Radio-labelled nucleotides may be employed as well. Then, nucleotides comprising $^{32}P$ or, in the case of a use of (gamma-thio)nucleotides, $^{35}S$, are employed. Thus, the corresponding radio-labelled peptides are obtained which contain at least the amino acid sequence of the alpha-hANaP (CDD-28).

It is possible, of course, to synthesize the compounds according to the invention by means of the Merrifield synthesis known to the artisan with the use of the appropriate phosphorylated components, for example phosphorylated serine, be it in radio-labelled or unlabelled form.

According to preferred embodiments, the peptide fragment R includes the amino acids 1–98 (for the peptide gamma-hANaP), 39–98 (for CDD-88) and 95–98 (for CDD-32, also designated as urodilatin).

An analytical method for the qualitative and/or quantitative determination of sodiuretic peptides derived from pre-pro-gamma-hANaP is feasible with the correspondingly radio-labelled peptides. According to the invention, those peptides are directly detected which possess at least the alpha-hANaP (CDD-28) sequence. The analytical detection of the physiologically active peptides of the pre-pro-gamma-hANaP is of diagnostic interest for differentiating certain clinical pictures by way of concentrations deviating from the average level in body fluids, for example in blood serum and in urine. For this purpose, a peptide having the formula II which is present in the the body fluid may be reacted, for example, with c-AMP-dependent proteinkinase or its catalytic subunit in the presence of radio-labelled nucleotide such as, e.g., [gamma-$^{32}P$]ATP or $^{35}S$-labelled or $^{32}P$-labelled adenosine-5'-(gamma-thio)triphosphate. In this embodiment, all physiologically active fragments containing at least the CDD-28 sequence of the pre-pro-gamma-hANaP are labelled. For carrying out the analytical method, the sample consisting of a body fluid or a tissue homogenate is prepared in a suitable manner by that, for example, in the former case they are forced through a non-polar matrix.

Then the samples are phosphorylated with the appropriate nucleotide in the presence of an enzyme such as c-AMP-dependent proteinkinase. The labelled fragment or pre-pro-gamma-hANaP itself is detected by means of known methods such as PAGE electrophoresis, urea gel electrophoresis with subsequent autoradiography or scintillation measurement, thin layer chromatography, high-voltage electrophoresis, isoelectrical focussing or HPLC (High Performance Liquid Chromatography) as well. Nevertheless, basically it is also possible to characterize the fractions isolated with the utilization of the labelled phosphorylated peptides in greater detail by using other biochemical or immunological methods (monoclonal antibodies).

The limit of detection may be lowered or the sensitivity of detection may be increased, respectively, either by the addition of larger amounts of the enzyme such as c-AMP-dependent proteinkinase or its catalytic subunit and/or by an extension of the incubation period, respectively, or by the use of nucleotides having a higher specific radioactivity. There is a considerable time-dependent loss of peptide material such as, for example, alpha-hANaP/CDD-28 due to absorption of the material on glass surfaces, which will be much reduced by the use of reaction vessels made of polyethylene. The c-AMP-dependent phosphorylation is capable of greatly changing the biological activity of peptide material. In the case of a additional determination of the substances by way of a bio-assay, thus it may be recommendable, depending on the circumstances, to use only [gamma-$^{32}P$]ATP as a co-substrate in the absence of the corresponding unlabelled ATP.

In a preferred embodiment of the invention, the use of the compound of the formula I results in a qualitative and/or quantitative determination of alpha-hANaP (CDD-28), CDD-32, CDD-88 and gamma-hANaP as well as pre-pro-gamma-hANaP.

Derivatives of the compound of the formula I according to the invention can be used as medicaments because of their physiological activities. In those cases in which the compounds according to the formula I have a physiological effect which is inferior to that of the corresponding actual active substances, the compounds according to the invention may be used to store the actual active substance according to the formula II as kind of a depot form. The compounds of the formula I are in vivo successively converted into their active forms due to the action of hydrolases, and especially of dephosphorylating enzymes (phosphatases).

The biological effects show that the phosphorylated peptide according to the formula I has a great clinical, diagnostic and therapeutic importance. More particularly, the compound according to the formula I is suitable to be used in the following fields of application: differentiated vasodilation of certain vessel beds, diagnostics and therapy of hypertonia, application as a substitution for patients, which have been implanted with artificial hearts, synchronous regulation of blood volume and electrolytes of the blood, skin diseases, and more particularly those including perspiration disorders, cardiovascular shock, renal and adrenal cortical disorders, diseases of the gastro-intestinal tract, and more particularly motility disorders and obstipation, therapy of brain edemae and of glaucoma, therapy of spastic coronaropathies such as angina pectoris, for the treatment of acute renal insufficiency, nephrotic and nephritic syndrome, terminal renal insufficiency, acute coronary insufficiency, ascites, generalized edemae, lung edema, brain edema, primary and secondary lymph edemae, hydrothorax, vena cava stenosis, hypoproteinemia, hearing impairment, essential and renal hypertonia, malignant hypertonia, EPH gestosis such as hypertonia of pregnancy, nephrosis of pregnancy, cerebral sodium storage syndrome, vessel spasms such as Morbus Raynaud, angina abdominalis, coronary spasms, coronary heart disease, vasomotor headache, headache upon hypertonia, Bing-Horton syndrome migraine, blood circulation disorders in the vertebralis-basilaris flow path region, disorders of the renin-angiotensin system, primary and secondary hyperaldosteronism, reninsecernent tumors, phaeochromocytoma, Bartter's syndrome, Schwartz-Bartter's syndrome, pancreatic insufficiency, primary sweat gland insufficiency such as anhidrosis, miction and defecation disorders, dysregulation of the anterior lobe of the pituitary gland, cardiovascular side-effects in the therapy of psychic diseases and agitation with catechol increase, for the supporting treatment upon heart transplantations, "PEEP-respiration" (an artificial respiration with positive end expiratory pressure) as well as by-pass operations and for the treatment of complications after implantation of an artificial heart.

The compound according to the formula I may also be employed as a diuretic for the treatment of multiple diseases such as gout combined with hypertonia/heart insufficiency, as well as diabetes with hypertonia/heart insufficiency, or as a diuretic in combination with cephalosporins, aminoglycosides or anticoagulants. Said compound is further suitable for the prophylaxis of an acute renal failure after kidney transplantations and treatment with nephrotoxic substances such as cyclosporin, cisplatin and ifosfamid and for the prophylaxis of an acute kidney failure which may occur postoperative or after hypertonic crisis as well as after dosis of contrast media for patients suffering from limited functions of the kidney. The agent according to the invention is also usable as a diagnostic for differential diagnostics of endothelial changes.

Therefore, subject matter of the invention is also medicaments containing the phosphorylated compound according to the formula I for use in the diagnosis and therapy methods as set forth above. The medicaments may be present in the conventional application forms for intravenous, oral or parenteral administrations, e.g., tablets, suppositories, dragées, solutions, sprays or preparations for inhalation etc., as well as micro-encapsulation, if desired in combination with conventional pharmacological excipients and/or diluents. The medicament according to the invention can also be formulated as slow-release-form. Preferably the amount of the active substance is from 50 ng to 50 µg per unit dose.

Furthermore, according to the invention there is provided a method for the specific determination of the compound according to the formula I, which method is based on the principle of immunoassay and employs an antibody directed against said compound. It has been determined that by using antibodies directed against the compound according to the formula I, cardiodilatin can be highly specifically and very accurately detected in body liquids. Said method for the specific determination of cardiodilatin can be used for the diagnosis of neurological diseases by specifically determining cardiodilatin or its fragments in the liquor cerebrospinalis.

The use of the medicament according to the invention which contains, as the active substance, the compound of the formula I, due to the beneficial spectrum of actions and low toxicity thereof, is indicated for the treatment of diseases involving disorders of the electrolyte and water balance such as, for example, preterminal and terminal renal insufficiency, malfunctions of the renin-angiotensin-aldosteron system, disorders of the vasopressin secretion, at liquid sequestration ("Third Space" problems such as ascites, glaucoma, brain edema, hydrothorax) as well as other diseases involving an increased extravasal volume accumulation such as lymph edema, EPH gestosis, vena cava stenosis, diseases involving hypoproteinemia such as renal diseases, enteropathies and liver diseases.

The medicament according to the invention, due to its vasodilative properties, may be used for the treatment of all diseases which are accompanied by an increased vasoconstriction. Thus, the medicament containing the compound according to the invention may be used for the treatment of spasms of vessels such as, for example, Morbus Raynaud, spasms of the muscular distributor arteriae and hearing impairment. The compound of the formula I may also be employed for treating further vascular diseases such as, for example, for the treatment of coronary heart disease, *Angina abdominalis*, vasomotor headache, *Arteria basilaris* migraine with blood circulation disorders in the vertebralis-basilaris flow path region and Bing-Horton syndrome.

The medicament according to the invention containing the compound having the formula I, due to its blood pressure-lowering properties which become effective above all with primarily increased blood pressure, is indicated for malignant hypertonia, and hypertonia of pregnancy, headache upon hypertonia, and hypertonia in combination with other diseases, for example gout and diabetes.

The medicament according to the invention exhibits antagonistic properties against sodium-retaining, water-retaining and vasoconstrictive hormones. This enables the use of the medicament according to the invention for the treatment of primary and secondary hyperaldosteronism, renovascular hypertony, renin-secernant tumors, phaeochromocytoma, Bartter's syndrome and Schwartz-Bartter's syndrome.

The medicament according to the invention containing the compound having the formula I can further be used for the treatment of heart insufficiency, in heart transplantations and with artificial hearts, for support in "PEEP" (positive end expiratory pressure), during bypass operations and with open heart surgery. In respiration with positive end expiratory pressure, expiration is effected against superatmospheric pressure.

The medicament according to the invention can be used for prophylaxis of acute renal failure after kidney transplantations, postoperatively and for improving the function of transplanted kidneys by pretreating the transplanted kidneys with the medicament of the invention.

The medicament according to the invention containing the compound having the formula I can also be used for diagnostic purposes. Since the vasodilation is endothel-independent, a comparison with an endothel-dependent vasodilator allows to make a statement on the condition of the endothel.

The use of the medicament according to the invention is also indicated at gastro-intestinal indications such as changes in the pancreas secretion and concomitant utilization disorders, nutritional defects, exocrine pancreas insufficiency, and regulations of bowels and bladder (miction and defecation disorders).

In dermatology, the medicament according to the invention may be used for combatting anhidrosis. Also in psychiatry the agent according to the invention may be used for the treatment of cardiovascular side-effects in the therapy of psych(iatr)ic diseases and agitation with catecholamine release.

These effects are observed already at concentrations within the nanomolar range. However, due to the low toxicity and good compatibility of the agent, higher concentrations may be injected or infused as well.

The compound having the formula I may be used for the preparation of medicaments such as solutions for injection or infusion, nasal spray, ophthalmic drops or as a slow-release form in the case of indications as mentioned above.

The examination of acute toxicity to animals has shown that in a dose range up to 400 µg/kg of body weight no toxic reactions do occur which are detectable using conventional control parameters (biochemistry). An $LD_{50}$ value is not determinable because of the low toxicity of the substance. No serious side-effects were observed in the heart-circulation system, bronchial system, liver and kidney function, gonads and central nervous system.

The pharmacological efficiency of a treatment of the above mentioned diseases ensues from the observed sodi-uretic effect which upon intravenous administration results in a rapid increase in diuresis and sodium excretion. Furthermore it has been observed that the compound having the formula I is capable of compensating the vasoconstrictive effect of noradrenalin.

It has further been observed that the substance inhibits the contracting effect of angiotensin. Of particular interest are cases of serious heart insufficiency with generalized edematosis which do not respond to a conventional therapy. Of considerable importance is also the action on the blood pressure-controlling systems and the vasopressin-controlling systems, so that functional disorders of the posterior lobe of the pituitary gland and psychotropic effects caused thereby are indicated. It is not to be excluded that a more intensive clinical investigation of this substance will result in that further interesting indications are found.

In a preferred embodiment of the invention, peptides comprising thiophosphate groups can be employed as depot forms in an especially advantageous manner, because these derivatives are only extremely slowly converted into the corresponding physiologically active equivalents.

BRIEF DESCRIPTION OF THE FIGURES

FIG. 3 shows an elution pattern of phosphorylated crude bovine atrial extract. Therein, aliquots of CDD-28 and CDD-88 that had been phosphorylated using the catalytic subunit of the c-AMP-dependent proteinkinase were separated by Reversed Phase HPLC on a TSK-ODS-120T column (300 mm×7.8 mm ID). The eluents employed were a) 0.01M hydrochloric acid, b) 0.01M hydrochloric acid in 80% aqueous acetonitrile. The flow rate was 1.5 ml/min. The solvent gradient is shown by the solid line obliquely extending through the graph. The optical density (—) was measured at 210 nm (absorption range 0.1). For the measurement of the radioactivity (.—.), 0.5 ml of each of the collected fractions were removed and counted.

FIG. 5 shows the effect of c-AMP-dependently phosphorylated ( - - - ) and unphosphorylated (—) CDD-28 onto the smooth vascular musculature. Muscle strips of rabbit aorta were first contracted by the action of a solution of norepinephrine ($10^{-7}$M). After constant conditions had been adjusted, the peptides were added (position of the arrow). The final concentration was from 0.3 to $0.6 \times 10^{-9}$M. The solid line shows the typical relaxation behavior in the presence of unphosphorylated CDD-28. The broken line, in contrast thereto, demonstrates the behavior after the application of phosphorylated CDD-28. Under these conditions, only a slight relaxation is detectable.

FIG. 8 shows the relative relaxation capability of phosphorylated and unphosphorylated CDD-32 (ANF/CDD-95-126; urodilatin). It is evident that the phosphorylated CDD-32, at a corresponding concentration, has a significantly lower relaxation capability than that of the unphosphorylated form. For the purpose of comparison, in FIG. 8 there has also been shown the corresponding ratio for the alpha-hANaP couple. It will be apparent therefrom that the phosphorylated compounds each have lower activities, corresponding to each other, than have the unphosphorylated parent compounds.

The invention is further illustrated by the following EXAMPLES:

EXAMPLE 1

Pre-purification of urine and serum samples (2 ml each) through SEP-PAK capsules (C-18 Cartridge, Waters Assoc., Millipore). The activation of the capsules (2 ml of triethylamine-methanol, 20:80), is followed by the application of 2 ml of sample volume and elution with 2 ml of the activating solution).

Reaction batch for the phosphorylation: 100 µl of the reaction batch contain 50 mM MOPS buffer (N-morpholino-3-propanesulfonic acid), pH 6.8, 10 mM of magnesium acetate, about 12.7 µg of the catalytic subunit of c-AMP-dependent proteinkinase (EC 2.7.1.37) from bovine heart (10 µl), serum or urine sample. The phosphorylating reaction is initiated by the addition of 2 mM ATP and [gamma-$^{32}$P] ATP (10 µCi/20 nmol of ATP) in 10 µl by mixing. The incubation is at 30° C. for 5 minutes. The concentration of the catalytic subunit may also be selected so that the complete phosphorylation is effected within from 5 to 40 minutes.

The phosphorylation reaction is terminated by shock-freezing in liquid nitrogen.

The separation of the phosphorylated reaction batch is done by way of HPLC via a TSK-ODS-120T column of the company Toyo Soda (300 mm×7.8 mm ID). A linear gradient of acetonitrile (from 0% to 80%) in 0.01N HCl is used for the elution. The absorption is measured at 210 nm. The collected volume of fractions is 1.5 ml. The incorporation of $^{32}$P is measured in 0.5 ml aliquots together with 2 ml of water in a scintillation counter (1 minute).

As the reference peptides there were employed synthetically prepared cardiodilatin-28 (CDD-28, Bissendorf Peptides Co.) and -32 (Bachem) as well as CDD-88 from bovine heart atria for the phosphorylation (Hock, D. et al, J. Chromatography 397 (1987), 347–353).

EXAMPLE 2

A further purification of the phosphorylated peptides by Reversed Phase HPLC may be carried out as follows: The reaction mixture obtained after the phosphorylation is applied to an RP column (Micropore, $C_{18}$, 4.6 mm×30 mm; Company Applied Biosystems). As the apparatus there may be employed an apparatus suitable for analytical HPLC such as that supplied by Applied Biosystems. Said apparatus is equipped with two pumps, a 1400 A-solvent-feeding system, a Spectroflow 491 Dynamic Mixer/Injector (0.2 ml sample loop) and a 1783 Absorbents Detector Collector. The column is first equilibrated with buffer A which contains 0.1% TFA (trifluoroacetic acid) and then developed with an increasing concentration of acetonitrile (buffer B: 70% of acetonitrile/ 0.09% TFA). The flow rate is 1 ml/min, and the absorption is measured at 220 nm. Chromatography is conducted at room temperature. Phosphorylated and unphosphorylated peptides elute under isocratic conditions as a uniform peak at an acetonitrile concentration of 24%. The fraction containing the phosphorylated peptides is collected, freeze-dried and stored at −70 ° C.

EXAMPLE 3

Purification of the phosphorylated peptides by cation exchange HPLC

The separation of the phosphorylated peptides, for example alpha-hANaP, is carried out by means of a cation exchanger column (4 mm×50 mm) with an HPLC apparatus from the company LKB, which is equipped with two pumps, a 2152 Controller, a 2151 Variable Wavelength Monitor and a Reodyne Injector (1 ml sample loop). The column is developed with a linear gradient with sodium chloride in 10 mM disodium hydrogenphosphate (pH 5) at a flow rate of 0.7 ml/min. The absorption is measured at 230 nm. The chromatography is carried out at room temperature. The initial sodium chloride concentration is 100 mM. The fractions containing the phosphorylated alpha-hANaP are determined by measuring the contained radioactivity. The relevant fractions are collected, freeze-dried and stored at −70 ° C. The sample can rid of the salt by means of a further Reversed Phase HPLC.

EXAMPLE 4

Bioactivity Tests

Aortae of New Zealand rabbits were prepared. The muscular tension was measured with a muscle strip in an organ bath containing physiological saline. The strips were precontracted with a solution of $10^{-6}$M of norepinephrin, then at fill relaxation. For the assay, a further contraction was induced with $10^{-7}$M of norepinephrin. After constant contraction conditions had been reached, the peptides were applied.

EXAMPLE 5

Effects of the phosphorylated alpha-hANaP on muscle relaxation

Alpha-hANaP was phosphorylated according to EXAMPLE 1 in the presence of ATP and the catalytic subunit according to EXAMPLE 1. For control, unphosphorylated alpha-hANaP was incubated under the same conditions, however in the absence of ATP. Phosphorylated and unphosphorylated alpha-hANaP were added to the precontracted rabbit aorta muscular strips, so that they were present in a final concentration of $0.3 \times 10^{-9}$M. The aorta muscular strip partially relaxes under the influence of the unphosphorylated peptides, whereas phosphorylated alpha-hANaP only produces a negligible effect. Stepwise addition of unphosphorylated, phosphorylated and in turn unphosphorylated alpha-hANaP allows clearly to recognize that only unphosphorylated alpha-hANaP exerts a significant relaxing effect in comparison to phosphorylated peptide. If the addition is reversed, first phosphorylated, then unphosphorylated and again phosphorylated alpha-hANaP, the corresponding reversed relaxation effect is found.

EXAMPLE 6

CDD-32 (Urodilatin) is phosphorylated according to Example 1 and investigated for its biological activity in the same manner as in Example 5. Urodilatin in the unphosphorylated state exhibits a dose-dependant relaxation activity with a stronger relaxing action at higher concentrations. Administration of phosphorylated urodilatin in corresponding concentrations causes a distinctly reduced relaxation.

We claim:
1. A purified compound having the formula I wherein X is a phosphate group or thiophosphate group and R is a residue —H or a peptide fragment from the amino acid sequence of gamma-hANaP.

2. The compound according to claim 1, wherein the peptide fragment R includes the amino acids 1–98, 38– 98 or 95–98 of the gamma hANaP.

3. The compound according to claim 1, wherein the phosphate group contains the isotope $^{32}$P.

4. The compound according to claim 1, wherein the thiophosphate group contains the isotopes $^{32}$P, $^{35}$S or both isotopes.

5. A process for preparing the compound according to claim 1, by chemical total synthesis according to the Merrifield method.

* * * * *

UNITED STATES PATENT AND TRADEMARK OFFICE
CERTIFICATE OF CORRECTION

PATENT NO. : 5,461,142
DATED : October 24, 1995
INVENTOR(S) : Forssmann et al

It is certified that error appears in the above-identified patent and that said Letters Patent is hereby corrected as shown below:

Column 2, line 11, change "$Tr^{126}$" to --$Tyr^{126}$--;

Column 2, line 29, change "$Tr^{126}$" to --$Tyr^{126}$--;

Column 3, line 63, change "a" to --an--;

Column 7, line 10, change "nANaP" to --hANaP--;

Column 8, line 3, change "alpha-nANaP" to --alpha-hANaP--; and

Column 10, claim 1, "$\begin{matrix} Cys \\ \lfloor S-S-S \rfloor \\ Cys \end{matrix}$" should be --$\begin{matrix} Cys \\ \lfloor S-S \rfloor \\ Cys \end{matrix}$--

Signed and Sealed this

Seventeenth Day of December, 1996

Attest:

BRUCE LEHMAN

Attesting Officer   Commissioner of Patents and Trademarks